United States Patent [19]

Suzuki

[11] Patent Number: 5,515,280
[45] Date of Patent: May 7, 1996

[54] ELECTRONIC CONTROL DEVICE FOR A MULTI-FUEL INTERNAL COMBUSTION ENGINE

[75] Inventor: Hiroyoshi Suzuki, Hyogo, Japan

[73] Assignee: Mitsubishi Denki Kabushiki Kaisha, Tokyo, Japan

[21] Appl. No.: 6,954

[22] Filed: Jan. 21, 1993

[30] Foreign Application Priority Data

Jan. 22, 1992 [JP] Japan .................................. 4-009238

[51] Int. Cl.⁶ .......................... G06G 7/70; F02D 41/00; C10L 1/18
[52] U.S. Cl. .................. 364/431.05; 364/431.04; 364/431.01; 123/1 A; 123/491; 123/494; 123/690; 123/689; 123/425; 123/434; 44/360; 44/449; 44/451; 44/352; 73/117.3
[58] Field of Search ................... 364/431.01–431.05, 364/424.1; 123/1 A, 416, 425, 494, 478, 689, 434, 575, 690, 685, 339.15, 491; 44/360, 352, 449, 459, 451; 73/117.3

[56] References Cited

U.S. PATENT DOCUMENTS

| | | | |
|---|---|---|---|
| 4,144,861 | 3/1979 | Yamashita et al. | 123/179 G |
| 4,438,749 | 3/1984 | Schwippert | 123/494 |
| 4,703,732 | 11/1987 | Wineland et al. | 123/416 |
| 4,706,629 | 11/1987 | Wineland | 123/478 |
| 4,706,630 | 11/1987 | Wineland et al. | 123/478 |
| 4,915,084 | 4/1990 | Gonze | 123/575 |
| 4,942,848 | 7/1990 | Terasaka | 73/117.3 |
| 4,945,863 | 8/1990 | Schmitz et al. | 123/494 |
| 4,971,015 | 11/1990 | Gonze | 123/494 |
| 5,015,091 | 5/1991 | Suzuki et al. | 356/135 |
| 5,146,882 | 9/1992 | Brinkman et al. | 123/1 A |
| 5,158,058 | 10/1992 | Yoshida et al. | 123/434 |
| 5,170,763 | 12/1992 | Kitajima et al. | 123/491 |
| 5,178,121 | 1/1993 | Kitajima et al. | 123/689 |
| 5,183,021 | 2/1993 | Suga et al. | 123/478 |
| 5,239,860 | 8/1993 | Harris et al. | 123/1 A |

*Primary Examiner*—Kevin J. Teska
*Assistant Examiner*—Jacques H. Louis-Jacques
*Attorney, Agent, or Firm*—Sughrue, Mion, Zinn, Macpeak & Seas; Richard C. Turner

[57] ABSTRACT

With an electronic control device for an internal combustion engine using an oxygenated compound mixed fuel, operating conditions of the engine are detected, and are utilized to determine fundamental control data for the engine, while the dielectric constant and the refractive index of an oxygenated compound mixed fuel supplied to the engine are detected, and the oxygenated compound content of the mixed fuel is calculated according to the dielectric constant thus detected. The refractive index, and the oxygenated compound content are utilized to estimate the distillation characteristic of the petroleum refined fuel in the mixed fuel. The fundamental control data are corrected by using first correction data determined from the oxygenated compound content and second correction data determined from the distillation characteristic. Thus, with the device, the engine operates stably and correctly at low and middle temperatures irrespective of the oxygenated compound content of the mixed fuel or the nature of gasoline thereof.

16 Claims, 10 Drawing Sheets

ELECTRONIC CONTROL DEVICE FOR A MULTI-FUEL INTERNAL COMBUSTION ENGINE

BACKGROUND OF THE INVENTION

1. Technical Field

This invention relates to an electronic control device performing a fuel control operation, an ignition control operation, and so forth for an internal combustion engine which uses a fuel obtained by mixing an oxygenated compound such as methanol, ethanol and MTBE (methyl tertiary butyl ether) with a petroleum refined fuel such as gasoline.

2. Background Art

Recently, in the United States of America and various European countries, in order to decrease the consumption of petroleum and to reduce the air pollution by exhaust gas from motor vehicles, a fuel prepared by mixing an oxygenated compound such as alcohol and ether with gasoline has been employed for motor vehicles. If such an oxygenated compound mixed gasoline is used, as it is, for an internal combustion engine matched with a gasoline fuel, then the engine suffers from the following difficulties: That is, methanol is appreciably different in theoretical air-fuel ratio from gasoline, about 6 to 15, and the former is larger in octane value that the latter, and the distillation characteristic depends on the methanol content. Hence, the operation of the engine is not satisfactory, and serious problems to be solved are involved in the driving characteristic of the engine and in the quantity of hazardous components exhausted therefrom. Thus, in controlling the operation of the engine, it is essential to detect the methanol content of the methanol mixed fuel.

An electronic control device for an internal combustion engine using an alcohol mixed fuel as an oxygenated compound mixed fuel has been disclosed by Japanese Patent Application (OPI) No. 98540/1981 or 51920/1982 (the term "OPI" as used herein means an "unexamined published application"). The conventional electronic control device is designed as follows: An alcohol content sensor is provided in the pipe through which an alcohol mixed fuel is supplied to the engine. That is, by detecting the dielectric constant (Japanese Patent Application (OPI) No. 98540/1981) or refractive index (Japanese Patent Application (OPI) No. 51920/1982) of the alcohol mixed fuel passing through it, the alcohol content of the alcohol mixed fuel is detected. The alcohol content thus detected is utilized to adjust the supply of the fuel thereby to control the air-fuel ratio, and to correct the ignition advance angle thereby to control the ignition timing.

That is, the fuel injection quantity is increased in proportion to the alcohol content to maintain the air-fuel ratio satisfactory. And, since alcohol is high in combustion speed, the ignition timing is, in general, delayed in proportion to the alcohol content. Furthermore, in the case of an alcohol mixed fuel, alcohol is lower in volatility than gasoline, and therefore the engine is unsatisfactory in starting characteristic when the temperature of the engine is in a range of low and middle temperatures. Hence, in the case when the temperature of the engine is in that range, especially at the start of the engine and immediately after it, control is made according to the alcohol content.

However, the above-described conventional electronic control device is disadvantageous in the following points: With the device, the operation of the engine is controlled only according to an alcohol content. Hence, in the case when the nature of gasoline mixed with alcohol changes, then the driving characteristic of the engine, and the quantity of hazardous components exhausted therefrom are adversely affected. That is, the volatility of an alcohol mixed fuel affecting the starting characteristic of an internal combustion engine depends not only on the alcohol content but also the volatility of the gasoline. The volatility of gasoline depends on the nature of distillation thereof. Under the condition that the temperature of the engine is in the above-described range of low and middle temperatures, the starting characteristic of the engine using a heavy gasoline low in volatility is lower than that of the engine using a light gasoline high in volatility.

On the other hand, the dielectric constant of an alcohol mixed fuel depends on the alcohol content, but it scarcely depends on whether the gasoline is a heavy one or whether it is a light one. On the other hand, the refractive index of the alcohol mixed fuel depends both on the alcohol content and the nature of the gasoline, but it is substantially free from whether the gasoline is a heavy one or whether it is light one. With a heavy gasoline low in volatility, or with a mixed fuel prepared by mixing alcohol with the heavy gasoline, the driving characteristic of the engine, and the amount of hazardous components exhausted therefrom are adversely affected, and at worst the engine cannot be started.

SUMMARY OF THE INVENTION

Accordingly, an object of the invention is to eliminate the above-described difficulties accompanying a conventional electronic control device for an internal combustion engine.

More specifically, an object of the invention is to provide an electronic control device for an internal combustion engine which, even when the oxygenated compound content of an oxygenated compound mixed fuel such as an alcohol mixed fuel, and/or the nature of a petroleum refined fuel such as gasoline therein changes, performs control operations so that the engine operates stably and correctly at low and middle temperatures.

According to one aspect of the invention, there is provided an electronic control device for an internal combustion engine using an oxygenated compound mixed fuel, the electronic control device includes: dielectric constant detecting means for detecting a dielectric constant of the oxygenated compound mixed fuel; refractive index detecting means for detecting a refractive index of the oxygenated compound mixed fuel; oxygenated compound content calculating means for calculating an oxygenated compound content of the oxygenated compound mixed fuel from the dielectric constant thus detected; distillation characteristic estimating means for estimating a distillation characteristic of the petroleum refined fuel in the oxygenated compound mixed fuel from the oxygenated compound content and the refractive index; and means for correcting fundamental control data by using first correction data determined from the oxygenated compound content, and second correction data determined from the distillation characteristic.

With the electronic control device, the dielectric constant and the refractive index of the oxygenated compound mixed fuel are detected. The oxygenated compound content is calculated from the dielectric constant thus detected, and the oxygenated compound content thus detected is utilized together with the detected refractive index to determine the distillation characteristic of the petroleum refined fuel in the oxygenated compound mixed fuel. And the first correction data determined from the oxygenated compound content, and the second correction data determined from the distillation characteristic are utilized to determine the fundamental correction data for the engine.

According to another aspect of the invention, there is provided an electronic control device for an internal combustion engine using an oxygenated compound mixed fuel, the electronic control device includes: refractive index detecting means for detecting a refractive index of the mixed fuel; oxygenated compound content calculating means for calculating an oxygenated compound content of the mixed fuel from the refractive index; means for controlling an air-fuel ratio for the engine so that it reaches an aimed air-fuel ratio; means for correcting the oxygenated compound content according to the difference between the aimed air-fuel ratio and the air-fuel ratio detected; distillation characteristic determining means for determining a distillation characteristic of the petroleum refined fuel of the mixed fuel from the oxygenated compound content thus corrected; and means correcting the fundamental correction data by using first correction data determined from the oxygenated compound content and second correction data determined from the distillation characteristic.

With the electronic control device, the refractive index of the mixed fuel is detected, and the refractive index thus detected is utilized to calculate the oxygenated compound content. The air-fuel ratio of the engine is so controlled that it reaches the aimed air-fuel ratio, and the oxygenated compound content is corrected according to the difference between the detected air-fuel ratio and the aimed air-fuel ratio. The oxygenated compound content thus corrected is utilized to estimate the distillation characteristic of the petroleum refined fuel in the mixed fuel. The first correction data determined from the oxygenated compound content, and the second correction data determined from the distillation characteristic are utilized to correct the fundamental control data for the engine.

The nature, principle, and utility of the invention will be more clearly understood from the following detailed description of the invention when read in conjunction with the accompanying drawings.

DETAILED DESCRIPTION OF THE PREFERRED EMBODIMENTS

Preferred embodiments of the invention will be described with reference to the case where an internal combustion engine uses a methanol mixed fuel in which the oxygenated compound is methanol.

First Embodiment

Figure 1:
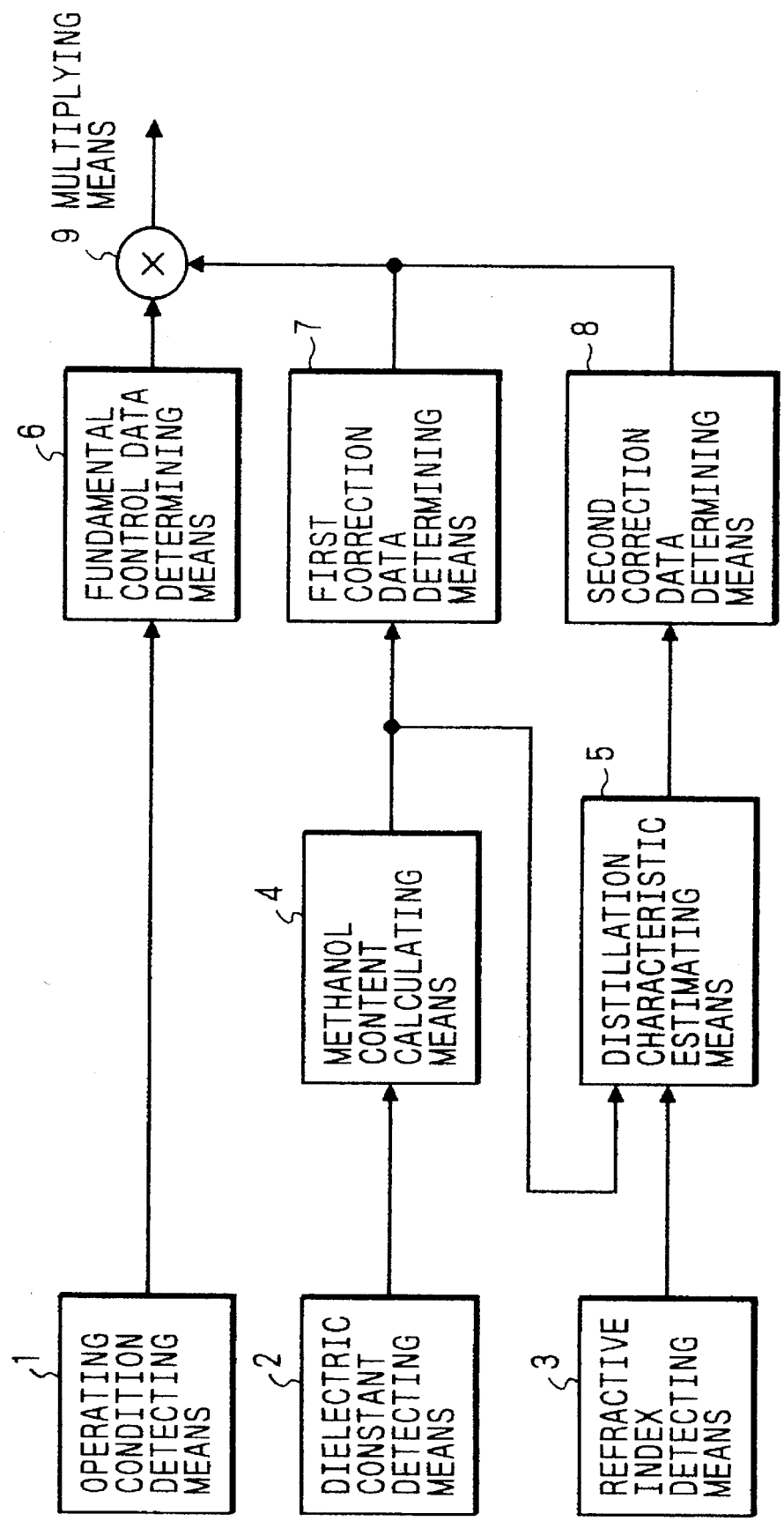
FIG. 1 is a block diagram showing the arrangement of an example of an electronic control device for an internal combustion engine, which constitutes a first embodiment of the invention.

An example of an electronic control device for an internal combustion engine, which constitutes a first embodiment of the invention, is designed as shown in FIG. 1. That is, the electronic control device of the invention includes: operating condition detecting means 1 for detecting an operating condition of the internal combustion engine which uses a fuel prepared by mixing methanol with a petroleum refined fuel; dielectric constant detecting means 2 for detecting a dielectric constant of a methanol mixed fuel supplied to the engine; refractive index detecting means 3 for detecting a refractive index of the methanol mixed fuel; methanol content calculating means 4 for calculating a methanol content of the mixed fuel from a dielectric constant detected by the dielectric constant detecting means 2; and distillation characteristic estimating means 5 for estimating a distillation characteristic of the petroleum refined fuel in the mixed fuel from a detection value provided by the refractive index detecting means 3 and a calculation value provided by the methanol content calculating means 4.

The electronic control device further includes: fundamental control data determining means 6 for determining fundamental control data of the engine according to the operating conditions detected by the operating condition detecting means 1; first correction data determining means 7 for determining first correction data according to the output of the methanol content calculating means; second correction data determining means 8 for determining second correction data according to an estimation value provided by the distillation characteristic estimating means 5; and multiplying means 9 for obtaining the product of the first and second correction data and fundamental control data determined by the fundamental control data determining means 6.

The arrangement of the electronic control device described above is shown in FIG. 2 concretely. That is, in FIG. 2, reference numeral 11 designates an internal combustion engine; 12, a speed sensor for detecting the speed of rotation of the engine 11; 13, a sucked-air flow rate sensor for detecting the flow rate of air sucked into the engine; 14, a throttle opening sensor provided for a throttle valve 22; 15, an air-fuel ratio sensor mounted on an exhaust pipe; 16, a dielectric constant sensor; and 17, a refractive index sensor. Those sensors 16 and 17 are provided in a high pressure pipe 27 downstream of a high pressure filter 28. Further in FIG. 2, reference numeral 18 designates a fuel injection valve which is coupled to a fuel distributing pipe 29 downstream of the sensors 16 and 17; 19, an ignition plug; 10, an electronic control section; 21, a cooling water temperature sensor; 24, an air cleaner; 25, a fuel tank; 26, a fuel pump; 20, a fuel pressure regulator; 30, a suction pipe; and 31, a return pipe.

Figure 3:
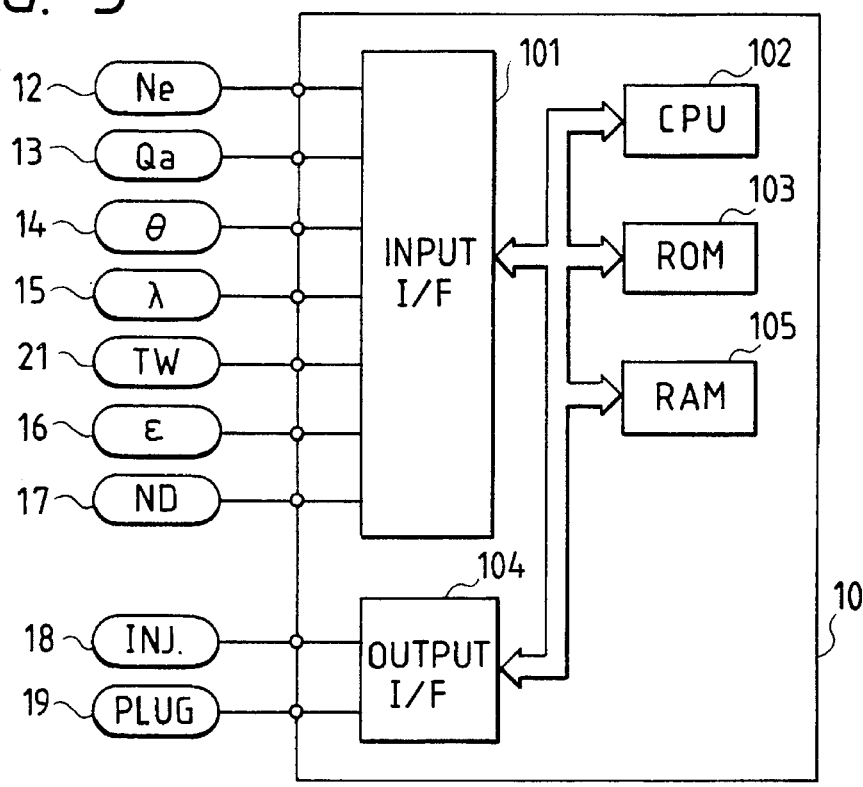
FIG. 3 is a block diagram showing the arrangement of an electronic control section in the electronic control device according to the invention.

The electronic control section 10 is as shown in FIG. 3. In FIG. 3, reference numeral 101 designates an input interface, to which the outputs of sensors 12 through 19 and 21 are applied; 102, a CPU (central processing unit); 103, a ROM (read-only memory); 104, an output interface for driving the fuel injection valve 18 and the ignition plug 19; and 105, a RAM (random access memory).

Now, the operation of the electronic control device shown in FIGS. 1 through 3 will be described.

Upon start of the engine 11, the methanol mixed fuel in the fuel tank 25 is pressurized by the fuel pump 26, so that it is supplied to the fuel distributing pipe 29 through the high pressure pipe 27 and the high pressure filter 28; while the dielectric constant sensor 16 and the refractive index sensor 17 detect the dielectric constant $\epsilon$ and the refractive index ND of the fuel, respectively, and apply them to the input interface 101 of the electronic control section 10.

The pressure of the fuel thus supplied is so controlled by the fuel pressure regulator 20 that it is constant irrespective to a quantity of fuel injected by the fuel injection valve 18, and the remaining fuel is returned into the fuel tank 25 through the return pipe 31. On the other hand, the operating conditions or data of the engine 11 are detected as follows: That is, the speed sensor 12 detects the speed of rotation Ne; the sucked-air flow rate sensor 13, the flow rate Qa of sucked air; the throttle opening sensor 14, the degree of opening $\theta$ of the throttle valve which represents the acceleration or deceleration of the engine; the air-fuel ratio sensor 16, the density $\lambda$ of exhaust gas; and the cooling water temperature sensor 21, the temperature TW of cooling water. The data thus detected are applied to the input interface 101 of the electronic control section 10.

According to a control program stored in the ROM 103, the CPU 102 controls the input interface 101 to read the operating data of the engine 11, and the dielectric constant $\epsilon$ and the refractive index ND of the fuel. The CPU 102 utilizes the operating data of the engine, to calculate fundamental control data for the fuel injection quantity of the fuel injection valve 18, and the ignition timing of the ignition plug 19; and utilizes the dielectric constant $\epsilon$ and the refractive index ND to calculate two correction data thereby to correct the fundamental control data. The CPU controls the output interface 104 according to the fundamental control data thus corrected, thereby to drive the fuel injection valve 18 and the ignition plug 19. In the above-described calculations, the RAM 105 is used to hold the data temporarily.

Figure 4:
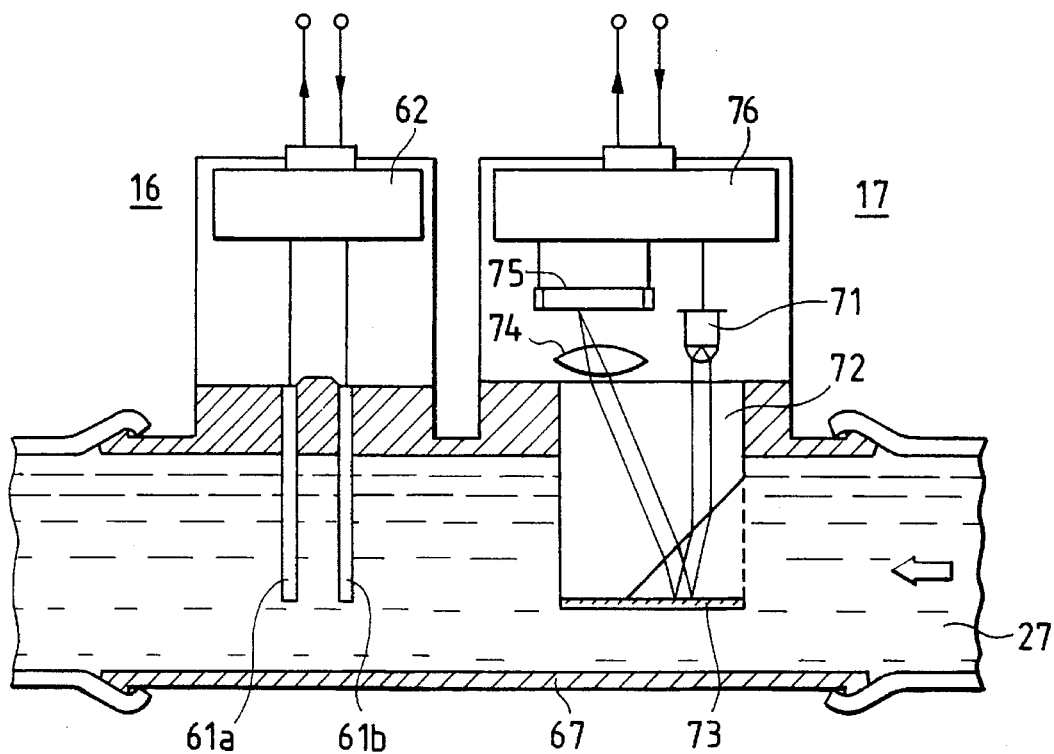
FIG. 4 is an explanatory diagram showing the arrangement of a dielectric constant sensor and a refractive index sensor in the electronic control device shown in FIG. 3.

The dielectric constant sensor 16 and the refractive index sensor 17 are designed as shown in FIG. 4.

Figure 6:
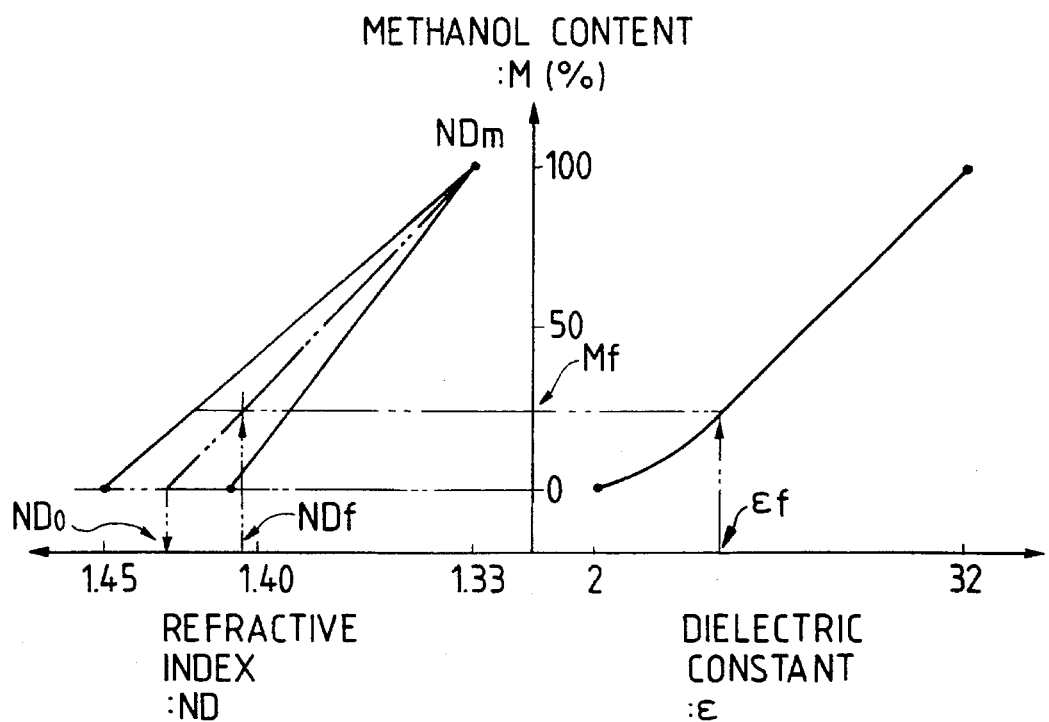
FIG. 6 is a graphical representation indicating relationships between dielectric constants, refractive indexes, and methanol contents for a description of the invention.

The dielectric constant sensor 16 includes a pair of electrodes 61a and 61b which are set in the fuel flow path formed in a pipe-shaped container 67 inserted in the high pressure pipe 27, thus forming a capacitor. As the methanol content M of the methanol mixed fuel flowing between the electrodes 61a and 61b increases, the dielectric constant $\epsilon$ is increased as shown in FIG. 6, and the capacitance C of the capacitor is also increased. The capacitance C is detected by a capacitance detecting circuit 62 made up of an LC oscillation circuit or RC oscillation circuit, as a result of which a signal corresponding to the dielectric constant $\epsilon$ of the fuel is outputted.

On the other hand, the refractive index sensor 17, as shown in FIG. 4, includes: a columnar prism 72 set in the fuel flow path in the pipe-shaped container 67. The prism 72 has a wetted surface at one end which is oblique with respect to the incident optical axis. The refractive index sensor 17 further comprises: a reflecting mirror 73 confronted with the wetted surface; an LED (light emitting diode) 71; a focusing lens 74; and a light position detecting element 75. Those components 71, 74 and 75 are provided on the side of the other end of the prism. When light is applied from the LED 71 to the columnar prism 72, then it is refracted at the wetted surface of the prism 72 at an angle of refraction corresponding to the refractive index of the fuel, and then reflected by the reflecting mirror 73. The light thus reflected is refracted at the wetted surface again in the same manner, thus passing through the columnar prism 72. As a result, it is focused on the light position detecting element 75 by the focusing lens 74.

As the refractive index ND of the fuel changes, the angle of refraction at the wetted surface of the columnar prism 72 is changed, and the optical path to the focusing lens 74 is therefore changed. As a result, the position of light focused on the light position detecting element 75 is changed. The position of light thus changed is detected by an light position detecting circuit 76, which outputs a signal corresponding to the refractive index ND of the fuel. The refractive index ND of the fuel depends not only on the methanol content M but also the nature of the gasoline with which methanol is mixed, as shown in FIG. 6.

Figure 5:
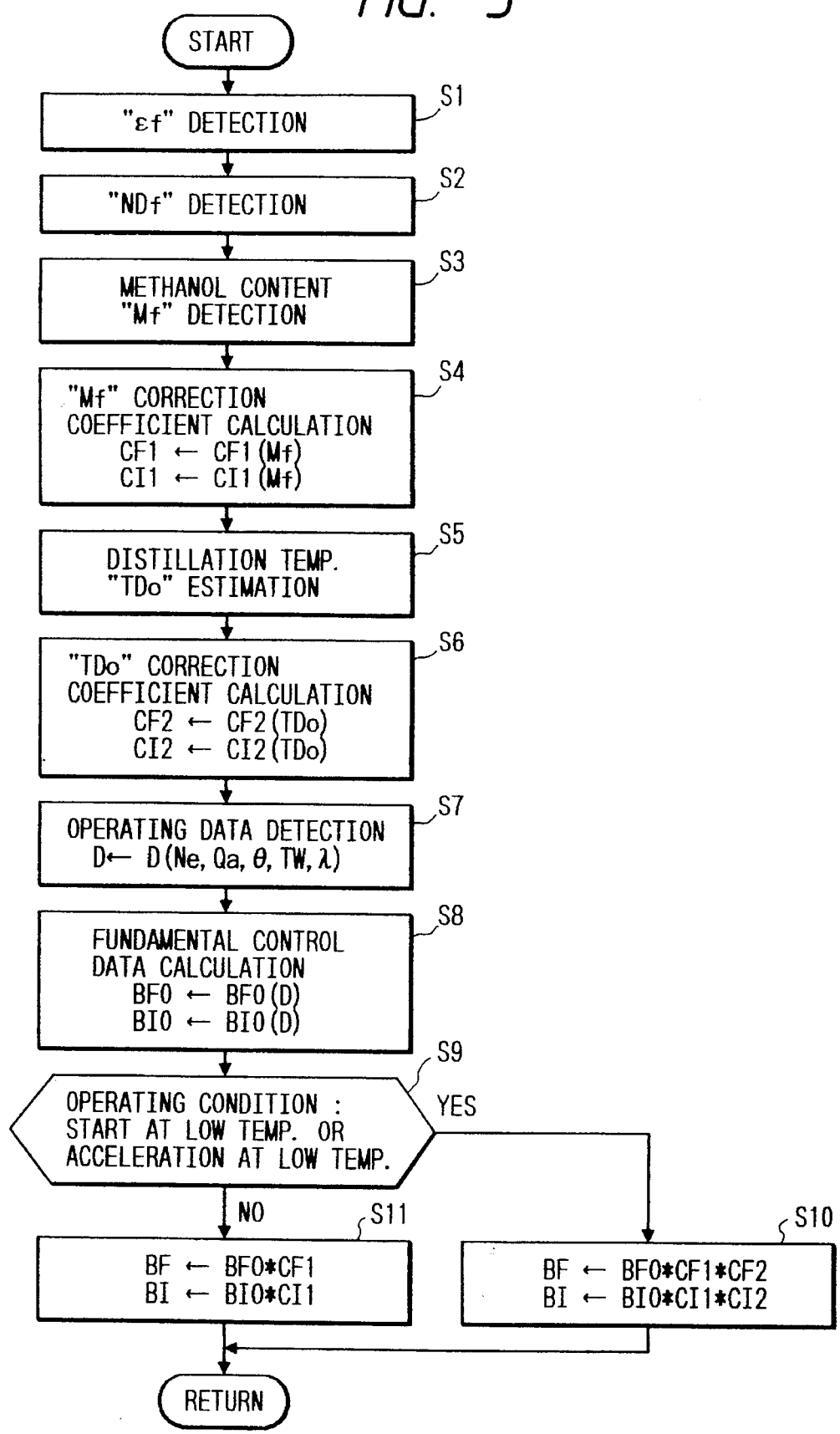
FIG. 5 is a flow chart for a description of the operation of the electronic control device according to the invention.

The operation of the electronic control section 10 will be described with reference to FIG. 5, a flow chart.

Upon start of the engine, the CPU 102 reads the dielectric constant $\epsilon$ of the fuel in Step S1, and reads the refractive index $ND_f$ of the fuel in Step S2. In Step S3, the CPU calculates a methanol content $M_f$ by using the relationships between dielectric constants $\epsilon$ and methanol contents M which are as shown in FIG. 6 and stored in the ROM 103. In Step S4, the CPU calculates first correction data CF1 and CI1 respectively for the fuel injection quantity and the ignition timing with respect to the methanol content $M_f$.

In Step S5, the methanol refractive index $ND_m$ stored in the ROM 103, the methanol content $M_f$ calculated, and the refractive index $ND_f$ detected are utilized to calculate according to the following Equation (1) the refractive index $ND_0$ provided when the methanol content is 0:

$$ND_0 = ND_m - 100*(ND_f - ND_m)/(M_f - 100) \tag{1}$$

Figure 7:
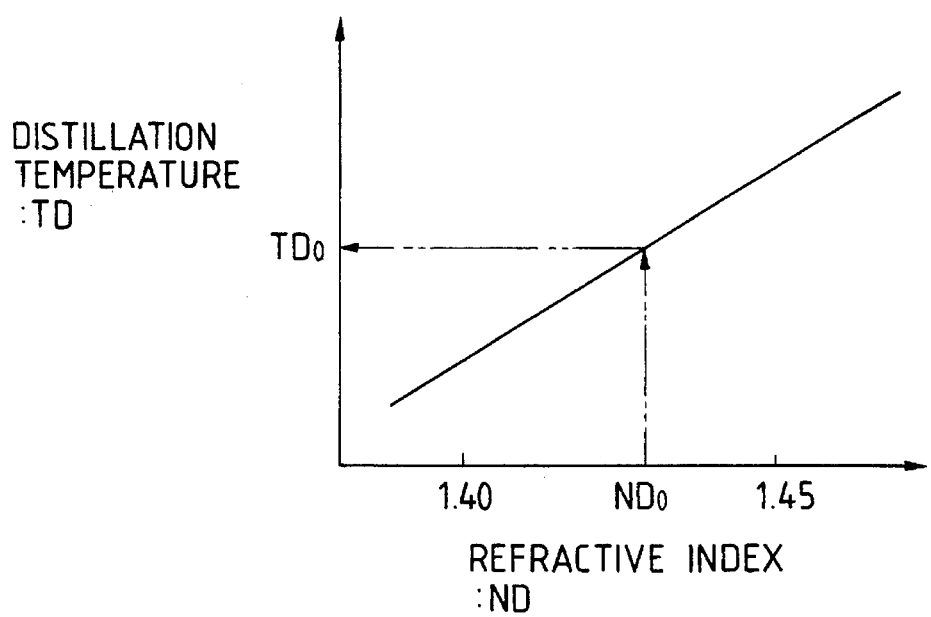
FIG. 7 is also a graphical representation indicating relationships between refractive indexes of gasoline and distillation temperatures of the same.

The relationships between distillation temperatures TD and refractive indexes ND as shown in FIG. 7, which are stored in the ROM 103, are utilized, to estimate a gasoline distillation temperature $TD_0$ with respect to the refractive index $ND_0$.

In Step S6, the distillation temperature $TD_0$ is utilized to calculate second correction data CF2 and CI2 respectively for the fuel injection quantity and the ignition timing.

As for the gasoline distillation temperature TD, it is suitable in correlation with the refractive index ND to use a 50% distillation temperature which concerns the driving characteristic of the engine most when the latter is at low and middle temperatures. It has been confirmed that, as shown in FIG. 7, the 50% distillation temperature is substantially proportional to the refractive index.

In this embodiment, the distillation temperature is an example of a representative quantity of the distillation characteristic. The distillation temperature indicates a temperature of a predetermined distillation ratio on a distillation ratio (%)—distillation temperature (°C.) curve, namely, the distillation characteristic. In addition to this, a distillation ratio which is a distillation at a predetermined distillation temperature can be applied as the representative quantity.

Figure 2:
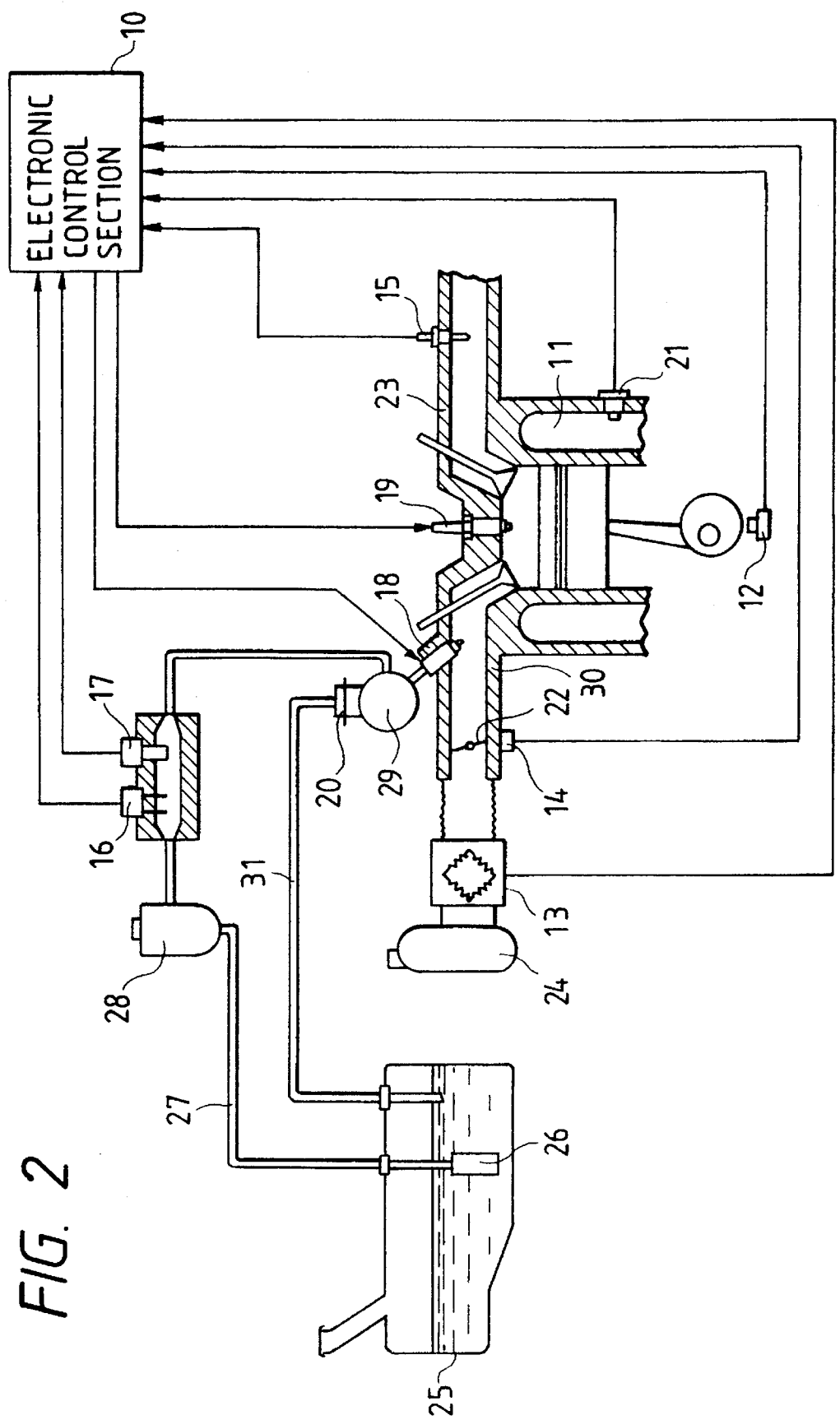
FIG. 2 is an explanatory diagram showing the arrangement of the electronic control device concretely.

In Step S7, the CPU receives operating data D (Ne, Qa, θ, λ and TW) from the operating data sensors 12 through 15 and 21 (FIGS. 2 and 3). In Step S7, the operating data D thus received are utilized to calculate fundamental control data for the fuel injection quantity and the ignition timing.

In Step S9, it is determined from the operating data D whether the engine performs a starting operation at low temperature start, or whether it performs an accelerating operation at low temperature, or else. When it is determined that the engine performs the starting operation at low temperature or the accelerating operation at low temperature, Step S10 is effected. In Step S10, the fuel injection quantity of the fuel injection valve 18, and the ignition timing of the ignition plug 19 are controlled according to the products of the fundamental control data and the first and second correction data. When the engine is in other operating conditions, in Step S11 the fuel injection quantity and the ignition timing are controlled according to the products of the fundamental control data and the first correction data.

The above-described first embodiment performs control operations as follows: In the case where the internal combustion engine using the methanol mixed fuel performs the starting operation at low temperature or the accelerating operation at low temperature which depends greatly on the volatility of gasoline, the fuel injection quantity of the fuel injection valve 18 and the ignition timing of the ignition plug 19 are correctively controlled by using not only the methanol content but also the distillation temperature of gasoline; i.e., the volatility of gasoline. When the engine is in other operating conditions: that is, the operating condition of the engine is scarcely affected by the volatility of gasoline, the fuel injection quantity and the ignition timing are correctively controlled by using only the methanol content. Hence, irrespective of the nature of the base material, gasoline, the engine is operated stably and suitably at all times, and the driving characteristic of the engine is improved while the quantity of hazardous components exhausted by the latter is decreased.

In the first embodiment described above, the engine uses the fuel prepared by mixing methanol with gasoline. However, it should be noted that the technical concept of the invention is applicable to the case where the engine uses a fuel which is prepared by mixing oxygenated compounds such as other alcohols and MTBE with a petroleum refined fuel, or the case where the engine uses a petroleum refine fuel mixed by nothing.

Furthermore, in the first embodiment, the dielectric constant sensor 6 and the refractive index sensor 7 are arranged in the high pressure pipe 27 downstream of the high pressure filter 28. However, they may be provided inside the fuel tank 25.

Second embodiment

Figure 8:
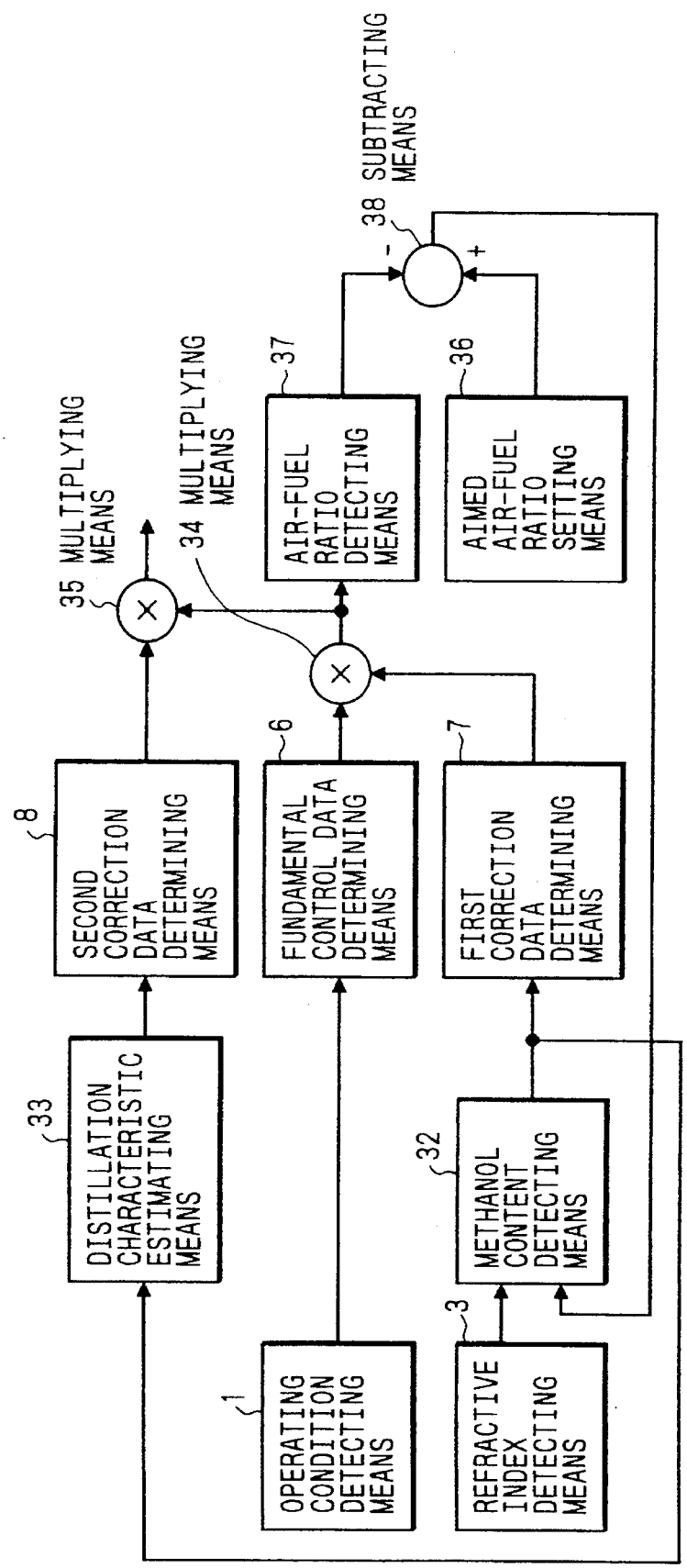
FIG. 8 is a block diagram showing the arrangement of another example of the electronic control device, which constitutes a second embodiment of the invention.

Another example of the electronic control device, which constitutes a second embodiment of the invention, as shown in FIG. 8, includes: methanol content calculating means 32 for calculating an methanol content of a methanol mixed fuel from a detection value outputted by refractive index detecting means 3; distillation characteristic estimating means for estimating an distillation characteristic of the petroleum refined fuel of a methanol mixed fuel from a calculation value provided by the methanol content calculating means; multiplying means 34 for obtaining a product of fundamental control data and first correction data; another multiplying means 35 for multiplying an output of the multiplying means 34 by second correction data; aimed air-fuel ratio setting means 36 for setting an aimed air-fuel ratio; air-fuel ratio detecting means 37; and subtracting means 38 for outputting the difference between the aimed air-fuel ratio and an actually detected air-fuel ratio, to correct the operation of the methanol content calculating means. The remaining parts are the same as those in the electronic control device shown in FIG. 1.

Figure 9:
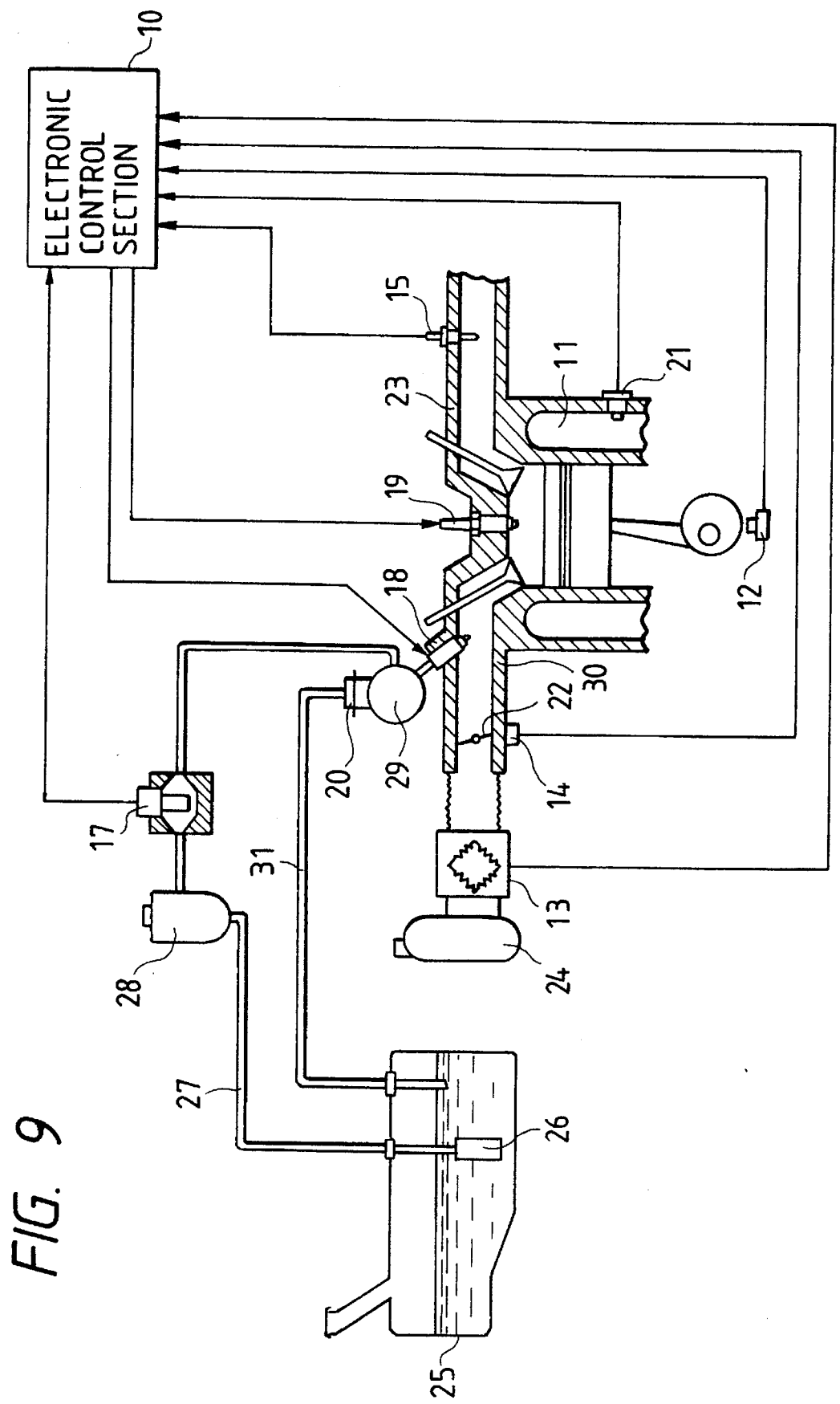
FIG. 9 is an explanatory diagram showing the arrangement of the second example of the electronic control device concretely.
Figure 10:
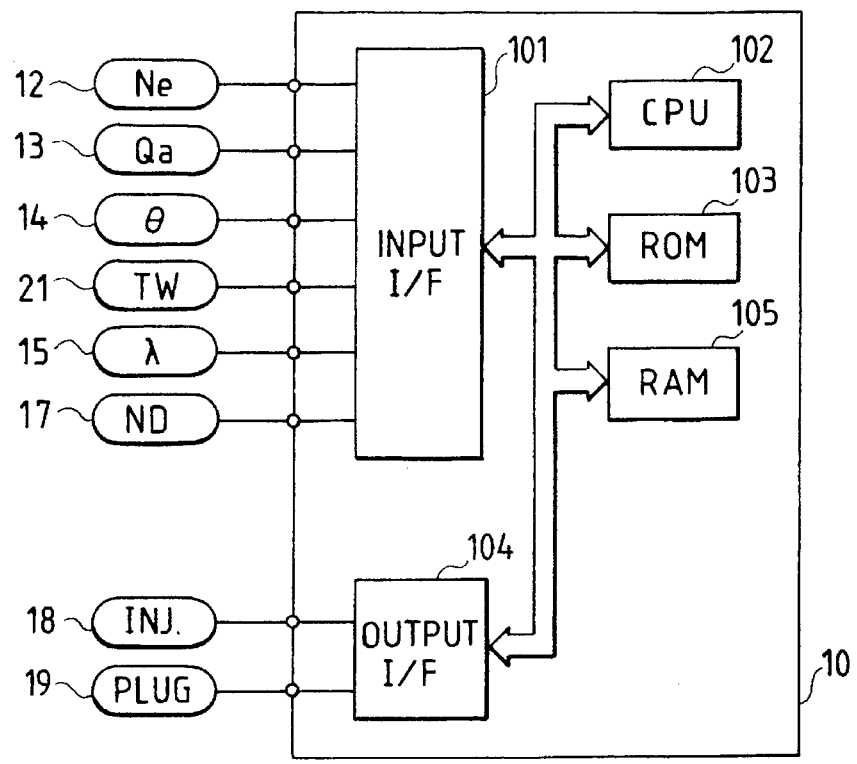
FIG. 10 is a block diagram showing the arrangement of an electronic control section in the electronic control device shown in FIG. 8.

The second example of the electronic control device is shown concretely in FIG. 9. As is apparent from comparison between FIGS. 9 and 2, the second example is different from the first example in that the dielectric constant sensor 16 is eliminated. The electronic control section 10 is as shown in FIG. 10. As is seen from FIGS. 10 and 3, the electronic control section 10 in FIG. 10 is substantially similar in arrangement to the one shown in FIG. 3.

The electronic control device shown in FIGS. 8 through 10 operates as follows:

When the engine 11 starts, the methanol mixed fuel in the fuel tank 25 is pressurized by the fuel pump 26, so that it is supplied to the fuel distributing pipe 29 through the high pressure pipe 27 and the high pressure filter 28; while the refractive index sensor 17 detects the refractive index ND of the fuel, and applies it to the input interface 101 of the electronic control section 10.

The pressure of the fuel thus supplied is so controlled by the fuel pressure regulator 20 that it is constant irrespective to a quantity of fuel injected by the fuel injection valve 18, and the remaining fuel is returned into the fuel tank 25 through the return pipe 31. On the other hand, the operating conditions of the engine 11, namely, the speed of rotation Ne, the flow rate Qa of sucked air, the degree of opening θ of the throttle valve, the air-fuel ratio λ, and the cooling water temperature TW are detected by the sensors 12 through 15 and 21. The data thus detected are applied to the input interface 101 of the electronic control section 10.

According to a control program stored in the ROM 103, the CPU 102 controls the input interface 101 to read the operating data of the engine 11, and the air-fuel ration λ and the refractive index ND of the fuel. The CPU 102 utilizes the operating data of the engine, to calculate a quantity of fuel injected by the fuel injection valve 18, and the ignition timing of the ignition plug 19, and calculates a methanol content from the air-fuel ratio λ and the refractive index ND, to obtain first correction data, and estimates the distillation characteristic of the gasoline from the methanol content, to obtain second correction data. The CPU corrects the fundamental control data by using the first and second control data, and applies the fundamental correction data thus corrected to the output interface 104, thereby to control the fuel injection quantity the fuel injection valve 18 and the ignition timing of the ignition plug 19.

Figure 11:
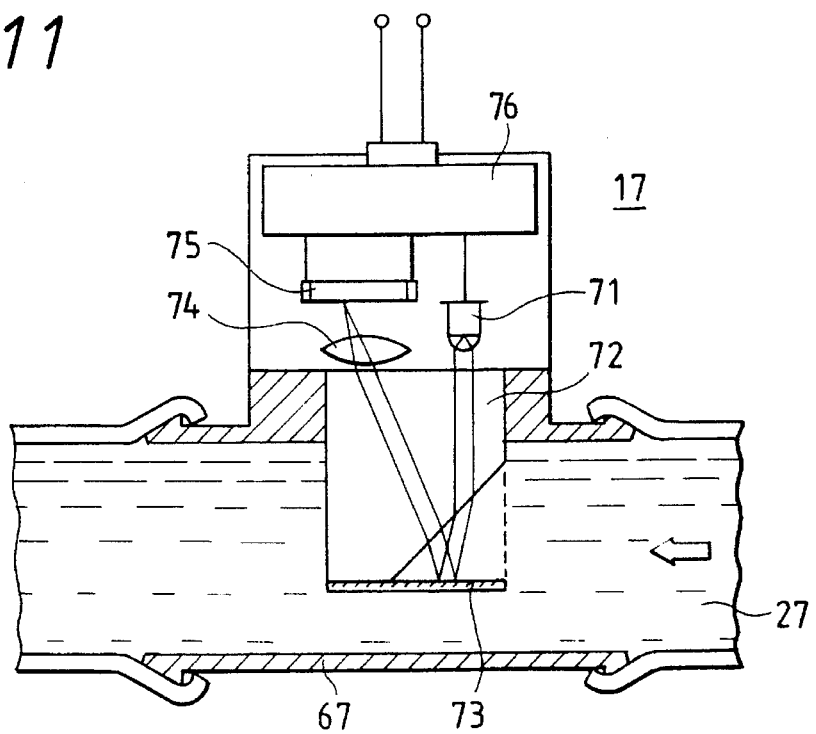
FIG. 11 is an explanatory diagram showing the arrangement of a refractive index sensor in the electronic control device shown in FIG. 9.
Figure 13:
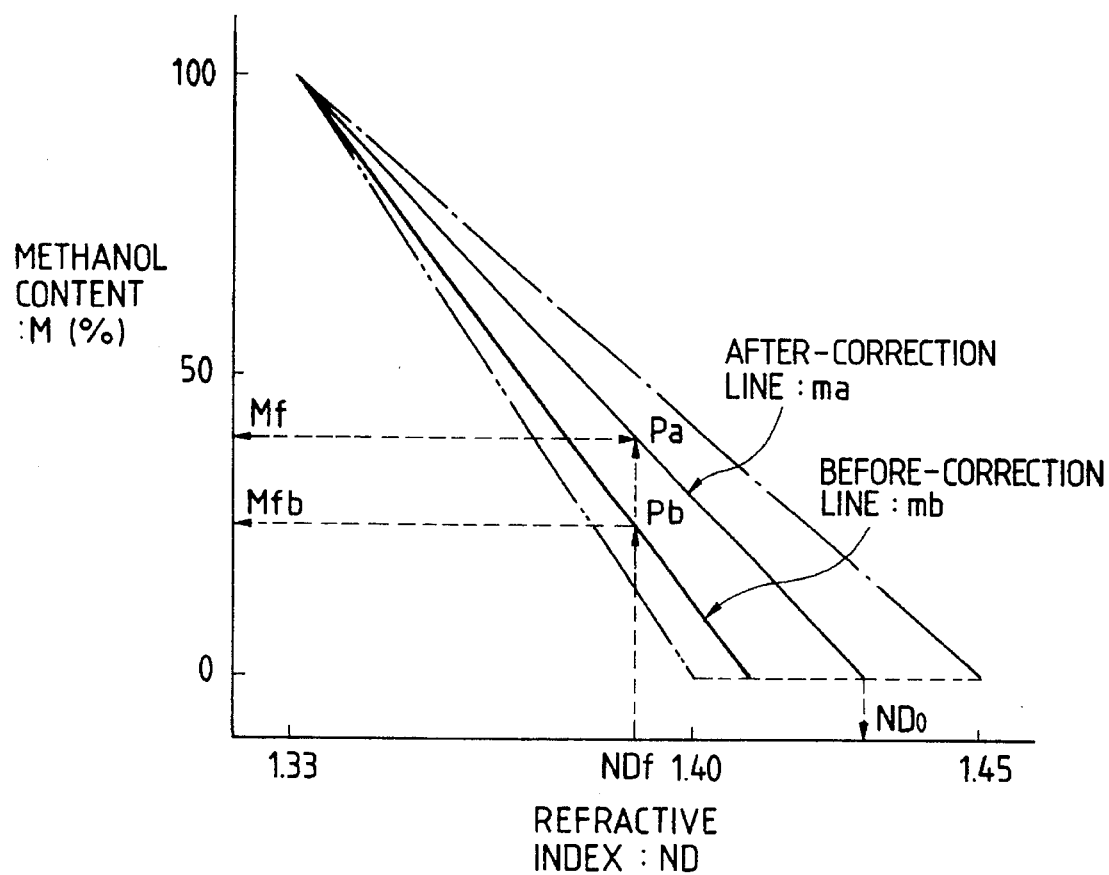
FIG. 13 is a graphical representation indicating relationships between refractive indexes and methanol contents for a description of the operation of the second example of the electronic control device according to the invention.

The arrangement of the refractive index sensor 17 is as shown in FIG. 11. As is apparent from comparison of FIGS. 11 and 4, FIG. 11 is obtained by removing the dielectric constant sensor 16 from FIG. 4. The operation of the sensor 17 is equal to that of the sensor 17 shown in FIG. 4. The refractive index ND of the fuel, as shown in FIG. 13, depends not only on the methanol content but also on the nature of gasoline.

Figure 12:
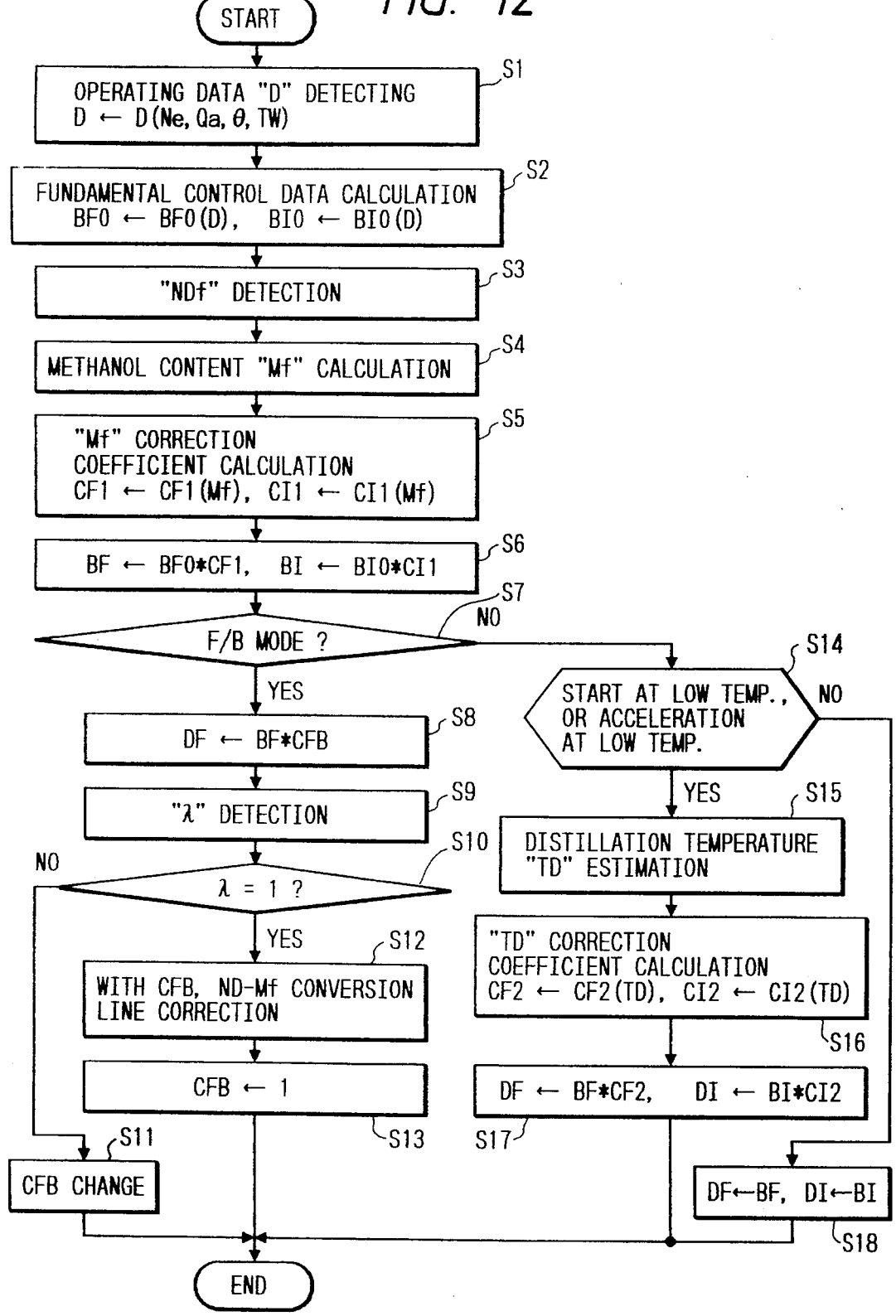
FIG. 12 is a flow chart for a description of the operation of the second example of the electronic control device according to the invention.

The operation of the electronic control section 10 will be described with reference to a flow chart of FIG. 12.

In Step S1, the CPU 102 controls the input interface 101 to read the operating data D (Ne, Qa, θ and TW) of the engine 11 from the sensors 12, 13, 14 and 21. In Step S2, the CPU utilizes the operating data D to calculate fundamental control data BF0 and BI0 respectively for the fuel injection quantity and the ignition timing.

In Step S3, the CPU reads the refractive index $ND_f$ of the fuel from the refractive index sensor 17. In Step S4, the CPU utilizes the relation (the line $ND_f$–$M_f$) between the refractive index and the methanol content of the mixture of methanol and gasoline having a predetermined nature which is stored in the ROM 103 in advance and indicated by the before-correction line "mb" in FIG. 13, thereby to calculate the methanol content $M_f$ from the $ND_f$ thus read. In Step S5, the CPU calculates first correction data CF1 and CI1 for the fuel injection quantity and the ignition timing with respect to the methanol content $M_f$. In Step S6, the fundamental control data BF0 and BI0 are multiplied by the first correction data CF1 and CI1, to provide correction control data BF and BI, respectively.

In Step S7, it is determined from the operating data D whether or not the supply of fuel is in an air-fuel ratio feedback mode. When it is determined that it is in the air-fuel ratio feedback mode, then in Step S8, the correction control data BF is multiplied by a feedback coefficient CFB, to provide fuel control data DF. The fuel control data DF thus provided is utilized to determine the period of time for which the fuel injection valve 18 is opened, thereby to control the fuel injection quantity. Initially, the coefficient CFB is set to one (1).

The operation of the electronic control device will be described with reference to the case where the actual nature of the base material, gasoline, is heavier than the nature of gasoline corresponding to the before-correction line "mb" which is stored in the ROM 103; that is, the gasoline is large in refractive index. In this case, the methanol content $M_{fb}$, which is obtained from the detected refractive index $ND_f$ by using the before-correction line "mb" stored in the ROM 103 is smaller than the actually detected methanol content $M_f$. Therefore, if the fuel injection is carried out with the value corrected by the data $M_{fb}$, then the fuel injection quantity becomes short because methanol is larger than gasoline in the quantity of fuel required for providing an ideal air-fuel ratio, and accordingly the air-fuel ratio becomes excessively small.

Hence, in Step S9, the output signal of the air-fuel ratio sensor 15 is read, and in Step S10 it is determined whether or not the air-fuel ratio λ is one (1) which is a theoretical air-fuel ratio. When λ is not one (1), in Step S11 the coefficient CFB is changed, and Step S1 is effected again. That is, in this case, the detected air-fuel ratio is extremely small. Therefore, the fuel injection quantity is increased by gradually increasing the coefficient CFB so that the air-fuel ratio λ reaches one (1).

Accordingly, when the air-fuel ratio λ is the theoretical value "1", the coefficient CFB corresponds to the ratio of the methanol content $M_f$ to the assumed methanol content $M_{fb}$. Therefore, in Step S12, the line $ND_f$–$M_f$ is modified with the actual methanol content $M_f$ corrected with the coefficient CFB, and is then stored as an after-correction line "ma" in the ROM 103 again. The coefficient CFB is reset in Step S13. That is, in Steps S1 through S13, the line $ND_f$–$M_f$ indicating the mixture of methanol and the base material gasoline is renewed at all times, so that the actual methanol content $M_f$ is obtained.

When, in Step S7, the air-fuel ratio feedback mode is not effected, Step S14 is effected. In Step S14, it is determined from the operating data D whether the engine 11 performs the starting operation at low temperature or the accelerating operation at low temperature, or else. When it is determined that the engine performs the starting operation at low temperature, Step S15 is effected. In Step S15, the line $ND_f$–$M_f$ "ma" stored in the ROM 103 is utilized to calculate the refractive index provided when the methanol content M is zero; i.e., the refractive index $ND_0$ of the base material, gasoline, as indicated in FIG. 13. And the distillation temperature $TD_0$ of the base material, gasoline, is estimated from the refractive index $ND_0$ with reference to FIG. 7 indicating the relationships between refractive indexes ND and distillation temperatures TD. In Step S16, the distillation temperature thus estimated is utilized to calculate second correction data CF2 and CI2 for the fuel injection quantity and the ignition timing with respect to the gasoline distillation temperature $TD_0$. Thereafter, in Step S17, the data BF and BI, which are obtained by correcting the fundamental control data with the first correction data corresponding to the methanol content, are corrected with the second correction data corresponding to the nature of the gasoline, so that the fuel injection valve 18 and the ignition plug 19 are suitably controlled.

As for the distillation temperature TD, in correlation with the refractive index ND it is suitable to employ a 50% distillation temperature which concerns the driving characteristic of the engine at low and middle temperatures greatly. It has been confirmed that, as shown in FIG. 7, the 50% distillation temperature is substantially in proportion to the refractive index. When the operation of the engine is not the start at low temperature nor the acceleration at low temperature, Step S18 is effected. In Step S18, control is performed by using the data obtained by multiplying the fundamental control data by the first correction data CF1 and CI1 corresponding to the methanol content.

In the second embodiment, in the case where the internal combustion engine using the methanol mixed fuel performs the starting operation at low temperature or of the accelerating operation at low temperature which depends greatly on the volatility of gasoline, the fuel injection quantity of the fuel injection valve 18 and the ignition timing of the ignition plug 19 are corrected by using not only the methanol content but also the distillation temperature of gasoline; that is, the volatility thereof. In the case where the operating the engine is other than the starting operation or accelerating operation at low temperature, thus being scarcely affected by the volatility of gasoline, the fuel injection quantity and the ignition timing are corrected by using only the methanol content. Therefore, the operating conditions of the engine can be maintained stable and suitable irrespective of the nature of the base material, gasoline, of the fuel. Accordingly, the driving characteristic of the engine is improved, and the quantity of hazardous components exhausted by the engine is reduced.

In the second embodiment, the theoretical air-fuel ratio sensor is employed as the air-fuel ratio sensor 15. However, the air-fuel ratio feedback may be carried out by using a wide range air-fuel ratio sensor capable of detecting air-fuel ratios in a wide range. In this case, the number of chances for renewing the line of refractive index vs. methanol content is increased, and the correction of data is improved in accuracy as much.

Similarly as in the first embodiment, the refractive index sensor 17 may be provided inside the fuel tank 25. In addition, fuels may be used which are prepared by mixing oxygenated compounds such as other alcohols and MTBE with a petroleum refined fuel. Alternatively, a petroleum refined fuel may be used as it is.

As was described above, with the electronic control device according to the first aspect of the invention, the operating conditions of the engine are utilized for determination of the fundamental control data of it. The first correction data are determined according to the oxygenated compound content which is calculated from the dielectric constant of the oxygenated compound mixed fuel, and the second correction data are determined according to the distillation characteristic which is estimated from the oxygenated compound content and the refractive index detected. The first and second correction data thus determined are utilized for correction of the fundamental control data. Hence, with the electronic control device of the invention, the engine operates stably and correctly at low and middle temperatures even when the oxygenated compound content or the nature of gasoline changes. Thus, the driving characteristic of the engine is improved, and the quantity of hazardous components exhausted from it is reduced.

Furthermore, with the electronic control device according to the second aspect of the invention, the fundamental control data of the engine are determined from the operating conditions of the latter, and the first correction data are determined from the oxygenated compound content which is calculated from the refractive index of the oxygenated compound mixed fuel which is supplied to the engine. The first correction data thus obtained are utilized to correct the fundamental control data so that the air-fuel ratio of the engine reaches the aimed air-fuel ratio. The oxygenated compound content is corrected according to the difference between the aimed air-fuel ratio and the actually detected air-fuel ratio. The oxygenated compound content corrected when the engine is in the predetermined operation mode, is utilized to estimate the distillation characteristic of the petroleum refined fuel in the mixed fuel, thereby to determine the second correction data. The first and second correction data thus obtained are utilized for correction of the fundamental control data. Hence, similarly, with the electronic control device, the engine operates stably and correctly at low and middle temperatures irrespective of the oxygenated compound content or the nature of gasoline. Thus, the driving characteristic of the engine is improved, and the quantity of hazardous components exhausted from it is reduced.

While there has been described in connection with the preferred embodiments of the invention, it will be obvious to those skilled in the art that various changes and modifications may be made therein without departing from the invention, and it is aimed, therefore, to cover in the appended claims all such changes and modifications as fall within the true spirit and scope of the invention.

What is claimed is:

1. An electronic control device for an internal combustion engine which can use a mixed fuel prepared by mixing oxygenated compound with a petroleum refined fuel, said electronic device comprising:

operating condition detecting means for detecting operating conditions of said internal combustion engine;

dielectric constant detecting means for detecting a dielectric constant of said mixed fuel;

refractive index detecting means for detecting a refractive index of said mixed fuel;

oxygenated compound content calculating means for calculating an oxygenated compound content of said mixed fuel from a detection value provided by said dielectric constant detecting means;

distillation characteristic estimating means for estimating a representative quantity of a distillation characteristic of said petroleum refined fuel in said mixed fuel from a detection value provided by said refractive index detecting means and a calculation value provided by said oxygenated compound content calculating means;

fundamental control data determining means for determining fundamental control data of said internal combustion engine from a detection value provided by said operating condition detecting means;

means for determining first correction data from said calculation value provided by said oxygenated compound content calculating means;

means for determining second correction data from an estimation value provided by said distillation characteristic estimating means; and means for correcting said fundamental control data with said first and second correction data.

2. The electronic control device according to claim 1, wherein said fundamental control data comprises data of a fuel injection quantity of said internal combustion engine and an ignition timing of an ignition plug of said internal combustion engine.

3. The electronic control device according to claim 2, wherein said operating condition detecting means detects whether said internal combustion engine is in one of a starting operation condition at low temperature, and an accelerating operation condition at low temperature.

4. The electronic control device according to claim 3, wherein said electronic control device correctively controls the fuel injection quantity and the ignition time of the ignition plug by using the oxygenated compound content of said mixed fuel and the distillation temperature of the petroleum refined fuel when said operating condition detecting means detects that said internal combustion engine is in one of said starting operation condition at low temperature and said accelerating operation condition at low temperature.

5. The electronic control device according to claim 3, wherein said electronic control device correctively controls the fuel injection quantity and the ignition time of the ignition plug by using the oxygenated compound content when said operating condition detecting means detects that said internal combustion engine is not in either of said operating conditions.

6. The electronic control device according to claim 1, wherein said operating condition detecting means comprises means for detecting a speed of rotation of said internal combustion engine, means for detecting a flow rate of air sucked into said internal combustion engine, means for detecting a throttle opening of said internal combustion engine, means for detecting an air-fuel ratio of said internal combustion engine and means for detecting a cooling water temperature of said internal combustion engine.

7. An electronic control device for an internal combustion engine which can use a mixed fuel prepared by mixing oxygenated compound with a petroleum refined fuel, said electronic control device comprising:

operating condition detecting means for detecting operating conditions of said internal combustion engine;

fundamental control data determining means for determining fundamental control data of said internal combustion engine from said operating conditions thus detected;

refractive index detecting means for detecting a refractive index of said mixed fuel;

oxygenated compound content calculating means for calculating an oxygenated compound content of said mixed fuel from said refractive index;

means for determining first correction data from said oxygenated compound content thus calculated;

first correcting means for correcting said fundamental control data by using said first correction data;

air-fuel ratio detecting means for detecting an actual air-fuel ratio of said internal combustion engine;

comparing means for comparing said actual air-fuel ratio and a target air-fuel ratio to obtain a difference value;

second correcting means for correcting said calculated oxygenated compound content according to said difference value;

distillation characteristic estimating means for estimating a representative quantity of a distillation characteristic of said petroleum refined fuel of said mixed fuel from said oxygenated compound content thus corrected and said refractive index;

means for determining second correction data from said distillation characteristic thus estimated; and means for utilizing said second correction data to correct said fundamental control data corrected with said first correction data.

8. The electronic control device according to claim 7, wherein said fundamental control data comprises data of a fuel injection quantity of said internal combustion engine and an ignition timing of an ignition plug of said internal combustion engine.

9. The electronic control device according to claim 8, wherein said operating condition detecting means detects whether said internal combustion engine is in one of a starting operation condition at low temperature and an accelerating operation condition at low temperature.

10. The electronic control device according to claim 9, wherein said electronic control device correctively controls the fuel injection quantity and the ignition time of the ignition plug by using the oxygenated compound content and the distillation temperature of the petroleum refined fuel when said operating condition detecting means detects that said internal combustion engine is in one of said starting operation condition at low temperature and said accelerating operation condition at low temperature.

11. The electronic control device according to claim 9, wherein said electronic control device correctively controls the fuel injection quantity and the ignition time of the ignition plug by using the oxygenated compound content when said operating condition detecting means detects that said internal combustion engine is in neither one of said operating conditions.

12. The electronic control device according to claim 7, wherein said operating condition detecting means comprises means for detecting a speed of rotation of said internal combustion engine, means for detecting a flow rate of air sucked into said internal combustion engine, means for a throttle opening of said internal combustion engine, and means for detecting a cooling water temperature of said internal combustion engine.

13. The device of claim 7 whereby said means for controlling said air-fuel ratio comprises a variable coefficient, whereby when said aimed air-fuel ratio is achieved, the value of said coefficient being correlated to the ratio of actual oxygenated compound content to said calculated oxygenated compound content and being communicated to said second correcting means so that a more accurate value of said calculated oxygenated compound can be obtained.

14. The device of claim 13 whereby said oxygenated compound content calculating means comprises predetermined data that correlate refractive indexes and compound contents, and said second correcting means uses said coefficient to update said predetermined data.

15. An electronic control device according to claim 7, further comprising means for controlling said air-fuel ratio of said internal combustion engine using the output of said first correcting means so that said air-fuel ratio reaches a target air-fuel ratio.

16. An electronic control device according to claim 13, wherein said difference value is the difference between said target air-fuel ratio and said air-fuel ratio thus detected.

* * * * *